(12) United States Patent
Middlesworth et al.

(10) Patent No.: US 7,834,236 B2
(45) Date of Patent: Nov. 16, 2010

(54) MULTILAYER WEB WITH EXTENSIBLE AND INEXTENSIBLE REGIONS AND METHODS OF MAKING SAME

(75) Inventors: Jeffrey Alan Middlesworth, Wauconda, IL (US); Stephen Donald Bruce, Montpelier, VA (US); Todd Richard Skochodopole, Moseley, VA (US); Matthew John O'Sickey, Powhatan, VA (US); Andrew James Peacock, Richmond, VA (US)

(73) Assignee: Tredegar Film Products Corp., Richmond, VA (US)

( * ) Notice: Subject to any disclaimer, the term of this patent is extended or adjusted under 35 U.S.C. 154(b) by 240 days.

(21) Appl. No.: 11/789,485

(22) Filed: Apr. 25, 2007

(65) Prior Publication Data
US 2007/0197990 A1    Aug. 23, 2007

Related U.S. Application Data

(62) Division of application No. 10/917,642, filed on Aug. 13, 2004, now abandoned.

(51) Int. Cl.
*A61F 13/15*    (2006.01)
*B29C 65/00*    (2006.01)

(52) U.S. Cl. ............ 604/378; 604/380; 604/385.101; 604/379; 604/385.26; 604/385.31; 604/365; 604/385.01; 156/164; 156/163; 156/161; 156/160

(58) Field of Classification Search ............... 604/378, 604/380, 385.101, 385.01, 379, 365, 385.26, 604/385.31; 442/183; 156/164, 163, 161, 156/160
See application file for complete search history.

(56) References Cited

U.S. PATENT DOCUMENTS

| | | | |
|---|---|---|---|
| 3,650,882 A | 3/1972 | Thomas | |
| 4,081,301 A * | 3/1978 | Buell | 156/164 |
| 4,606,964 A | 8/1986 | Wideman | |
| 4,747,846 A * | 5/1988 | Boland et al. | 604/385.22 |
| 5,376,198 A | 12/1994 | Fahrenkrug et al. | |
| 5,545,158 A | 8/1996 | Jessup | |
| 5,576,090 A | 11/1996 | Suzuki | |
| 5,683,787 A | 11/1997 | Boich et al. | |
| 5,769,993 A | 6/1998 | Baldauf | |
| 5,797,895 A | 8/1998 | Widlund et al. | |
| 5,846,232 A | 12/1998 | Serbiak et al. | |
| 5,882,769 A | 3/1999 | McCormack et al. | |

(Continued)

*Primary Examiner*—Jacqueline F. Stephens
(74) *Attorney, Agent, or Firm*—Joseph A. Tessari (57) ABSTRACT

A multi-layered web is provided that includes an elastic web bonded to an inelastic web. The inelastic web has extensible and inextensible regions arranged along the machine direction. In the extensible regions, the inelastic web is bonded to the elastic web in a creped structure that is extensible by virtue of the creping. A continuous process is provided to manufacture a multi-layer web having extensible regions that are conjoined with regions that are inextensible by varying the tension that is applied during manufacture of the multi-layer web. The apparatus comprises an elastic web that is fed into a bonding nip, into which one or more inelastic webs are also provided. The elastic web is fed into the bonding nip under a tension that is alternated between a low value that is sufficient to ensure processing stability, and a higher value that provides an elongation to the elastic web. During the low tension phase of the bonding process the inextensible region is formed in the multi-layer web due to the inextensibility of the web.

5 Claims, 6 Drawing Sheets

U.S. PATENT DOCUMENTS

| | | |
|---|---|---|
| 6,159,587 A | 12/2000 | Perdomi |
| 6,472,084 B1 | 10/2002 | Middlesworth et al. |
| 6,481,483 B1 | 11/2002 | Kobayashi et al. |
| 6,531,207 B1 | 3/2003 | Eaton et al. |
| 6,635,136 B2 | 10/2003 | White et al. |
| 2003/0134094 A1 | 7/2003 | Zafiroglu et al. |
| 2003/0135189 A1 | 7/2003 | Umebayashi |
| 2003/0217803 A1 | 11/2003 | Hermansson et al. |
| 2003/0226634 A1 | 12/2003 | Gardner |
| 2004/0013850 A1 | 1/2004 | Kling |
| 2004/0044323 A1* | 3/2004 | Roessler et al. ........ 604/385.24 |
| 2004/0118892 A1* | 6/2004 | Weber et al. ................... 226/44 |

\* cited by examiner

MULTILAYER WEB WITH EXTENSIBLE AND INEXTENSIBLE REGIONS AND METHODS OF MAKING SAME

This application is a divisional application of U.S. patent application Ser. No. 10/917,642 filed on Aug. 13, 2004.

BACKGROUND

Certain embodiments relate to disposable articles for hygiene applications, for example articles that comprise elastic waistpanels that stretch in the machine direction (MD). Other embodiments relate to multi-layered webs that form waistpanels and processes for manufacturing the multi-layered webs.

Absorbent articles such as diapers, training pants or incontinence garments exist that are configured to provide a close, comfortable fit about the wearer and contain body exudates while maintaining skin health. Many conventional absorbent articles employ elastic materials in the waist section of the article in order to secure the article around a wearer. Absorbent articles may also employ various elastic configurations, such as waist elastics, leg elastics, elasticized liners, and elasticized outer covers. Fasteners and elastic components have been employed to help produce and maintain the fit of the articles about the body contours of the wearer as well as provide containment and comfort.

Skin health is promoted by reducing the humidity of the air that trapped between the absorbent article and the skin of the wearer. In an attempt to reduce the humidity level within such absorbent articles, breathable polymer films have been employed as outer covers for such absorbent articles. The breathable films are typically constructed with pores to provide desired levels of liquid impermeability and air permeability. Other absorbent article designs have been proposed to provide breathable regions in the form of breathable panels or perforated regions in otherwise vapor-impermeable outer covers to help ventilate the articles.

The elastic materials used in absorbent articles may be laminated to one or more soft webs in order to further improve the appearance and comfort of the article. In particular, non-woven fiber webs have found extensive use in this area, as they have a soft feel and exhibit porosity values that are compatible with the breathability requirements of the application.

However, there remains a need for soft materials that are elastic in only certain specific regions of the waist area of an article, but inelastic in other regions, yet can be manufactured economically.

BRIEF SUMMARY OF THE EMBODIMENTS

In accordance with at least one embodiment, a multi-layered web is provided that includes an elastic web bonded to an inelastic web. The inelastic web has alternately extensible and inextensible regions along the machine direction. In the extensible regions, the inelastic web is bonded to the elastic web in a creped structure that is extensible by virtue of the creping.

Optionally, the multi-layered web may be porous and either of the elastic or inelastic webs may comprise a multiplicity of holes or micropores. Optionally, the elastic laminated web may comprise a porous elastic film and a nonwoven web.

In accordance with another embodiment, a continuous process is provided to manufacture a multi-layer web having extensible regions that are conjoined with regions that are inextensible by varying the tension that is applied during manufacture. The multi-layer web comprises an elastic web that is fed into a bonding nip, to which one or more inelastic webs are also provided. The elastic web is fed into the bonding nip under a tension that is alternated between a low value that is sufficient to ensure processing stability, and a higher value that provides an elongation to the elastic web. During the low tension phase of the bonding process the inextensible region is formed in the multi-layer web due to the inextensibility of the web.

Optionally, the inelastic web may be creped in certain creped regions prior to bonding with the elastic web to create extensibility in the creped regions.

In accordance with an alternative embodiment, an absorbent article is provided having one or more laminated webs of the structures and formed in according to the methods discussed herein. Examples of absorbent articles include pull-on garments, pants, diapers and the like.

DETAILED DESCRIPTION OF THE EMBODIMENTS

The term "porosity" shall mean the porosity of a material to vapor or gas. The term "porous" shall mean having a porosity of at least approximately 1.0 ($m^3/m^2$/min). The porosity testing can be performed on a Textest FX 3300 (Advanced Testing Instruments Corp., SC) equipped with a 20 $cm^2$ orifice with a test pressure of 125 Pa.

The term "holes" shall mean discrete openings that join and extend between opposite surfaces of the web. The term "micropores" shall mean passageways through the web where the passageways have dimensions that are measured in microns and may comprise bending, tortuous paths through the web. A web with holes may be produced by numerous processes, for example, the holes may be produced by a vacuum forming process that inserts apertures into the plane of the film. Alternatively, the holes may be produced by other means, such as knives or blades positioned on a roller over which the film or laminate is passed.

The term "creped" shall mean a web material having arcuate structures extending from one surface and that are continuous with the surface of the material. A corrugated structure is an example of one creped structure. A creped structure shall include a structure in which the portion of the arcuate portions of the structure does not extend from one edge of the web to the other. For example, the arcuate portions of the structure may have the appearance of "molehills" when viewed under a magnifying lens. No limitation on the size of the arcuate structures is implied by the use of the term "creped".

The term "elastic" shall refer to materials having at least 80% recovery from 50% elongation. A material shall be considered inelastic when it does not exhibit 80% recovery once elongated 50%. Inelastic materials break or are permanently damaged when stretched beyond 50% elongation. As an example only, recovery testing may be performed by stretching a sample that is 25.4 mm wide with a gauge length of 50.8 mm to the "test elongation" at 508 mm/minute, at which extension it is held for 30 seconds and then allowed to relax at 508 mm/minute to 0% extension at which it is held for 60 seconds, and then stretched at 508 mm/minute. The permanent set is the elongation of the sample at which the load cell first detects a load in excess of 1 Newton on the second extension. The percent recovery is calculated as 100× ("test elongation"−"permanent set")/"test elongation". For example, consider a length of material that was 10 inches in length in a normal resting state not under tension. When the length of material is elongated 50%, it is stretched to 15 inches. The material is then released and permitted to return to a resting state. If the material contracts to a length of 11 inches or less, it is considered to have 80% recovery.

The term "machine direction" shall mean a direction within a plane of the elastic web that is parallel to the long dimension of the elastic web at the time that the elastic web is either being formed or fed into a converting process during production of an article. For example, when the multi-layer web is being formed, component webs of the multi-layer web are fed or conveyed along one or more paths to a bonding station. The multi-layer web is conveyed from the bonding station along a discharge path. When the multi-layer web moves away from the bonding station it moves in a direction that corresponds to the machine direction. The multi-layer web has a width laterally transversing the bonding station and oriented perpendicular to the machine direction.

The term "extensibility" shall refer to the amount of strain, expressed as a percentage relative to the zero strain state, that may be applied to a web by a tensile force without breakage of fibers or bonds between fibers if the web has a fibrous structure, or yielding of material that the web comprises if the web is a continuous material such as a film. For a non-woven web to be extensible in a given direction means that when a tensile force is applied to the web in the given direction, the web expands in the given direction, and a strain is induced in the web, substantially without breakage of fibers, or of bonds between fibers. A web may be creped in order to increase its extensibility. The extensibility of a creped web has two components, namely the "intrinsic extensibility" and the "crepe induced extensibility". The "intrinsic extensibility" refers to the extensibility of the web in its natural, uncreped, state. The "crepe induced extensibility" refers to the strain that can be applied to extend the web in a given direction by virtue of the creping structure. For example, after a creped web has been stretched by the full extent permitted by the "crepe induced extensibility," the web is essentially in an uncreped state.

The terms "extensible configuration" and "inextensible configuration" define whether a web, be it single or laminated to another web, is extensible or not. For example, a non-elastic web held in a flat state is in an inextensible configuration. However, when the non-elastic web is creped to introduce a "crepe induced extensibility", then the creped non-elastic web is in an extensible configuration.

As used herein, the term "absorbent article" denotes articles that absorb and contain fluids and other exudates. More preferably, an absorbent article includes garments that are placed against or in proximity to the body of a wearer to absorb and contain the various exudates discharged from a body. A non-exhaustive list of examples includes absorbent towels, diapers, training pants, absorbent underpants, adult incontinence products, feminine hygiene products and the like.

Figure 1:
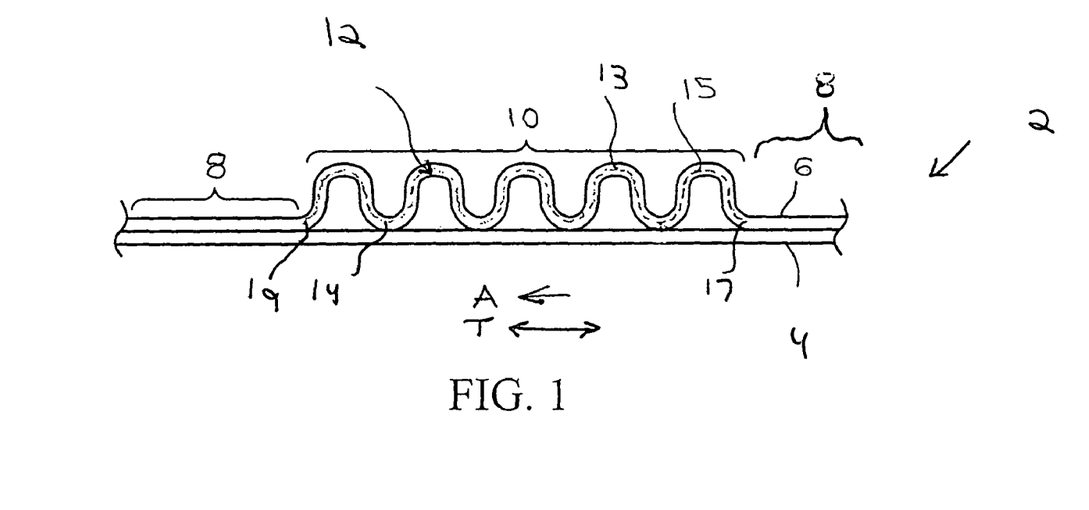
FIG. 1 illustrates a cross section of a multi-layer web formed in accordance with an embodiment.

FIG. 1 illustrates a cross section of an elastic multi-layer web 2 formed in accordance with an embodiment. The multi-layer web 2 comprises an elastic web 4 and an inelastic web 6 bonded together in a face to face relationship. The inelastic web 6 comprises alternating inextensible regions 8 and extensible regions 10. The inextensible regions 8 of the inelastic web 6 are bonded to the elastic web 4. The bonding may be at discrete points, or in a continuous pattern depending on the method of bonding chosen. Examples of bonding methods include thermal bonding, adhesive lamination and ultrasonic bonding. The inextensible regions 8 are characterized in that, when a tensile force is applied to the inextensible regions 8 along the directions shown by the arrow T in FIG. 1, the inextensible regions 8 only extend as far as permitted by the intrinsic extensibility of the inelastic web 6.

The extensible region 10 of the inelastic web 6 shown in FIG. 1 includes a creped structure 12 that allows the multi-layer web 2 to be extensible. The creped structure 12 includes a series of peaks 13 and valleys 14 arranged in an undulating or wavy pattern. The overall uncreped length (denoted by dashed line 15) of the material forming the creped structure 12 follows and wraps through each peak 13 and valley 14 between transition points 17 and 19 spaced apart in the machine direction A. The overall uncreped length 15 of the extensible region 10 is more than the creped length of extensible region 10. In the example of FIG. 1, the extensible region 10 of the inelastic web 6 is creped. Optionally, the extensible region 10 may be rendered extensible through other means besides creping. The inelastic web 6 may be bonded to the elastic web 4 at either discrete points or continuously in regions where the creped structure 12 of the inelastic web 6 meets the elastic web 4. For example, bonds may be formed at valleys 14 within the creped structure 12 at discrete points or continuously in the transverse direction along the width of the multi-layer web 2.

Figure 2:
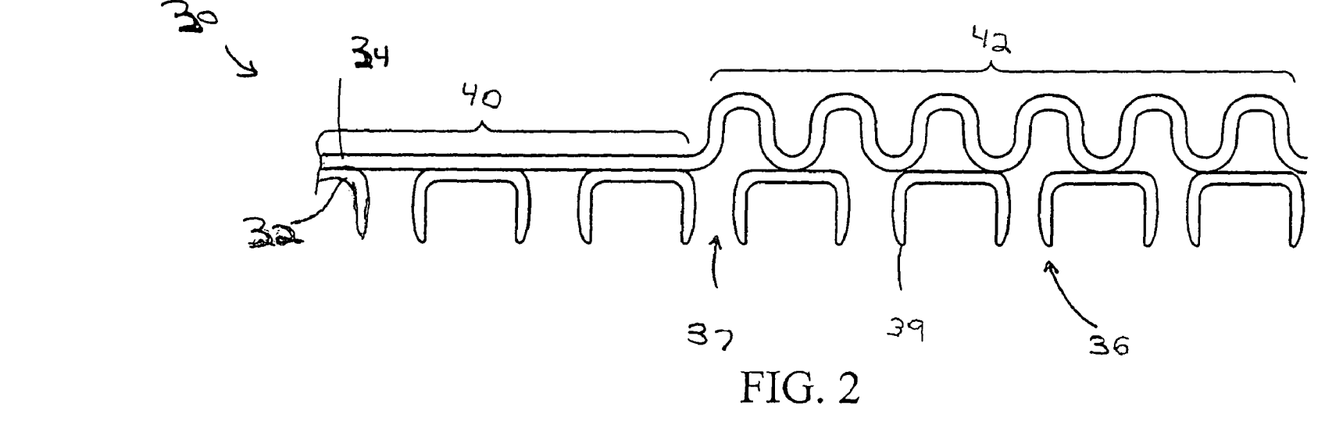
FIG. 2 illustrates a cross section of a multi-layer web formed in accordance with an alternative embodiment.

FIG. 2 illustrates a cross sectional view of a multi-layer web 30 formed in accordance with an alternative embodiment, in which the multi-layer web 30 is porous. The multi-layer web 30 includes an elastic web 32 and an inelastic web 34 bonded together in a face to face relationship. The inelastic web 34 is formed from a porous non-woven material. The elastic web 32 in the example of FIG. 2 is a perforated vacuum formed film which is porous and contains a plurality of cones 36 and holes 37. Optionally, the elastic web 32 may comprise holes 37 that are formed by cutting, for example slits or other shapes, or by hydroforming. Optionally, the multi-layer web 30 may comprise one or more non-woven webs (not shown) laminated to the exposed side 39 of the elastic web 32. The holes 37 in the elastic web 32 of FIG. 2 may vary in size and shape to provide a desired porosity. The holes 37 may be arranged in the plane of the elastic web 32 in various patterns, for example in a regular repeating pattern, or a random pattern. The inelastic web 34 comprises alternating inextensible regions 40 and extensible regions 42 formed continuous with one another along a longitudinal axis 44 corresponding to the machine direction.

Figure 3:
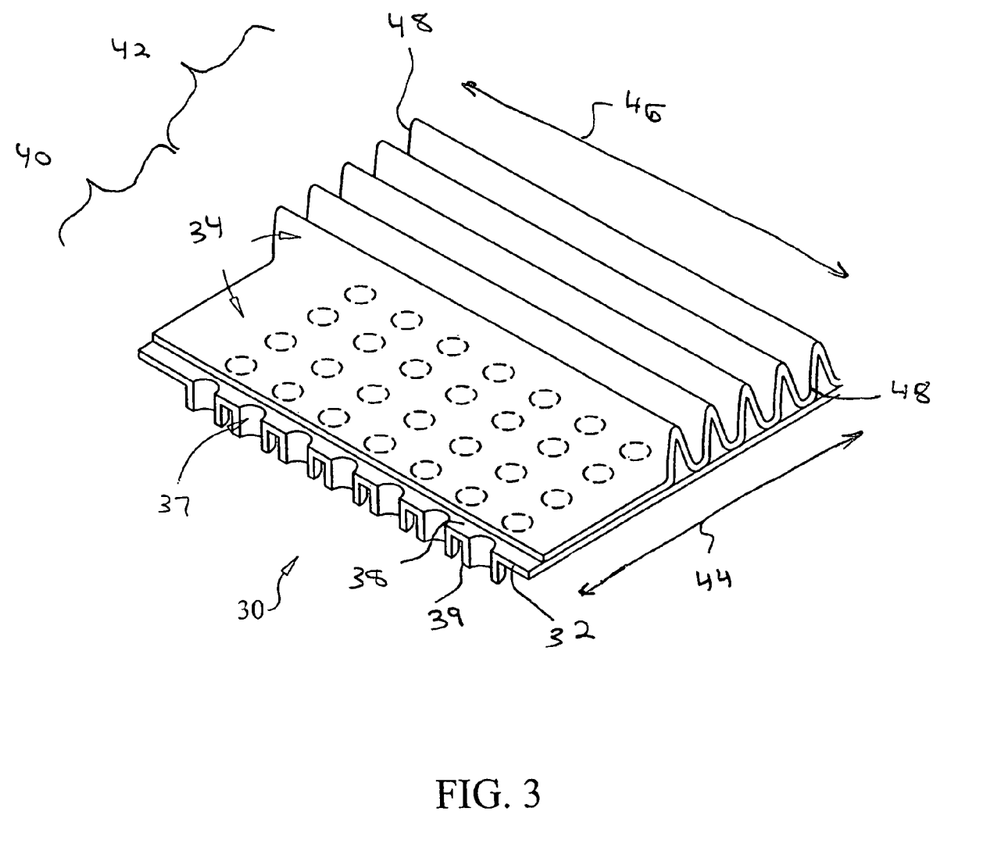
FIG. 3 illustrates a perspective view of a full width of the multi-layer web of FIG. 2.

FIG. 3 illustrates a perspective view of the multi-layer web 30 of FIG. 2. The elastic web 32 has an exposed side 39 and a covered side 38. The holes 37 extend entirely through the elastic web 32 between the exposed and covered sides 39 and 38. The inelastic web 34 is bonded to the covered side 38 of the elastic web 32. The inelastic web 34 may be formed of a non-woven material and the like. The inelastic web 34 is constructed with regions having different levels of extensibility. The multi-layer web 30 is constructed to have a length extending in the direction of longitudinal axis 44 and a width extending in the direction of transverse axis 46. The multi-layer web 30 has sides 48 and the inelastic web 34 is constructed with the extensible region 42 extending along the entire transverse axis 46 between the sides 48. Hence, the extensible region 42 of the inelastic web 34 is extensible across the entire width of the laminated web 30 between sides 48. The inextensible region 40 also extends across the entire width of the laminated web 30. Hence, the multi-layer web 30 is extensible across the entire width of the extensible region 42 and is inextensible across the entire width of the inextensible region 40.

Figure 4:
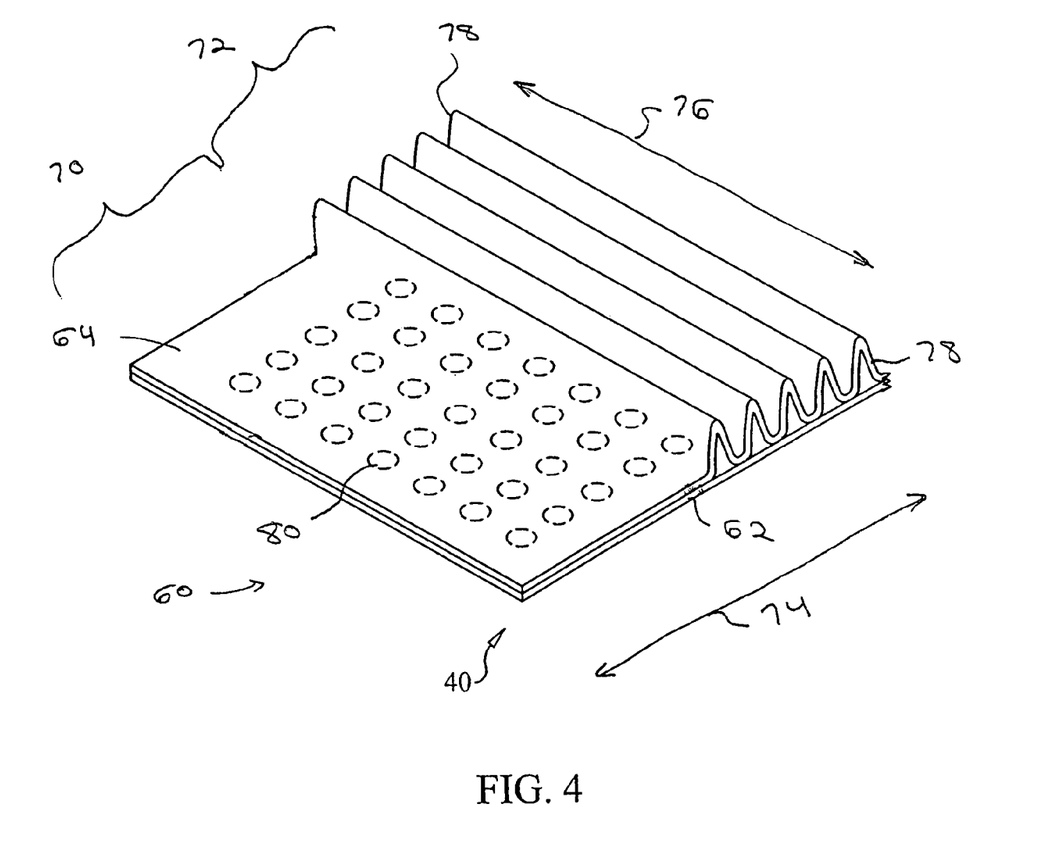
FIG. 4 illustrates a perspective view of a full width of a multi-layer web formed in accordance with an embodiment.

FIG. 4 illustrates a perspective view of an alternative embodiment of a laminated web 60 formed with an elastic film 62 bonded in a face to face relation to an inelastic web 64. The inelastic web 64 has an inextensible region 70 and an extensible region 72 located adjacent one another along the longitudinal axis 74 (corresponding to the machine direction). The inextensible region 70 extends across an entire width along transverse axis 76 of the laminated web 60 between sides 78. The extensible region 72 also extends across the entire width of the laminated web 60 along transverse axis 76 between sides 78. An array of holes 80 is illustrated in dashed lines. The holes 80 are cut through the thickness of the elastic film 62, but do not extend through the inelastic web 64. The holes 80 may have a variety of shapes and be arranged in a variety of patterns to provide a desired porosity and without unduly changing the mechanical strength of the elastic film 62.

Figure 5:
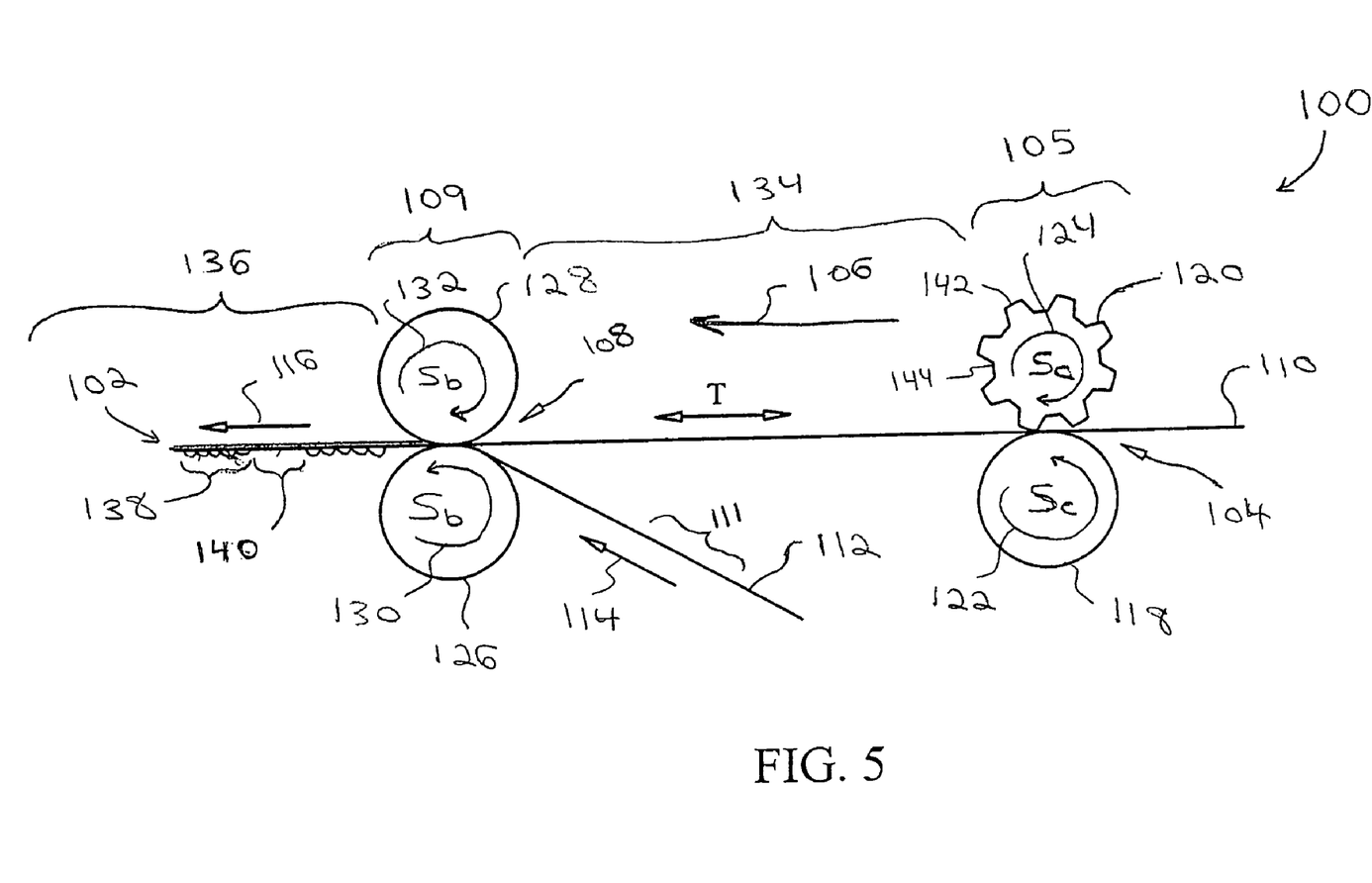
FIG. 5 illustrates an apparatus for producing a multi-layer web in accordance with an embodiment.

FIG. 5 illustrates an apparatus 100 for producing a multi-layer web 102 in accordance with an embodiment. The apparatus 100 includes a gripping nip 104 located at a gripping station 105 which is upstream along a machining direction 106 of a bonding nip 108 located at a bonding station 109. An elastic web 110 is first fed into the gripping nip 104 and then through a staging area 134 and into the bonding nip 108. The bonding nip 108 bonds the elastic web 110 with an inelastic web 112 which is fed to the bonding nip 108 in the direction of arrow 114 also through the staging area 134. The elastic and inelastic webs 110 and 112 are joined (e.g., laminated) in the bonding nip 108 to produce the multi-layer web 102 which is conveyed downstream in the direction of arrow 116.

The bonding nip 108 includes smooth rollers 126 and 128 that are located proximate one another and rotate in opposite directions 130 and 132 at a feed rate or linear circumferential speed Sb. The gripping nip 104 includes a smooth roller 118 and a grooved roller 120 proximate one another. The grooved roller 120 alternately grips and releases the elastic web 110 at a frequency and for durations that define the size and position of the extensible regions 138 and inextensible regions 140 of the multi-layer web 102. The smooth and grooved rollers 118 and 120 rotate in opposite directions 122 and 124, respectively, at a feed rate or linear circumferential speed Sc. The speed Sb of the bonding nip 108 is greater than the speed Sc of the gripping nip 104.

The gripping nip 104 alternates between "open" and "closed" states or positions as the roller 120 rotates. The roller 120 is formed with a plurality of protruding ribs 142 and grooves 144 that extend across the width of the roller 120 in the transverse direction (corresponding to the transverse axes 46 and 76 in the embodiments of FIGS. 3 and 4). The grooves 144 in roller 120 are at least as wide as the width of the elastic web 110. When a groove 144 from roller 120 is positioned immediately adjacent the roller 118, the elastic web 110 is released. When a rib 142 from roller 120 is positioned immediately adjacent the roller 118, then the elastic web 110 is gripped. Each rib 142 rotates through a gripping region immediately adjacent the roller 118, at which region the rib 142 and roller 118 grasp the elastic web 110. The gripping nip 104 is in a closed state when gripping the elastic web 110, thereby controlling the feed rate at which the elastic web 110 passes through the gripping nip 104 (e.g., speed Sc). Once a rib 142 passes through the gripping region, the rib 142 disengages and releases the elastic web 110.

Optionally, in one embodiment, the roller and grooves may be wider than the film width, but the grooves are narrower than the roller overall width. The portion of the roller that extend laterally beyond the grooves will form a "collar" along side each edge of the grooves. The collar engages and rides on the opposed smooth roller at all times, thereby keeping the smooth and grooved rollers positioned in a desired manner with respect to one another.

When the gripping nip 104 is closed, the elastic web 110 is advanced from the gripping nip 104 at a speed Sc which is less than the speed at which the multi-layer web 102 is discharged from the bonding nip 108. Hence, when the gripping nip 104 is closed, a tension T is introduced into the elastic web 110 along the staging area 134. The tension T is sufficient to elongate the elastic web 110 such that, when the elastic web 110 is gripped at the bonding nip 108, the inelastic web 112 is bonded to the elastic web 110 while the elastic web 110 is under tension T. The portion of the elastic web 110 in the staging area is elongated to a length that corresponds to the overall uncreped length (see length 15 in FIG. 1). When the multi-layer web 102 is discharged from the bonding nip 108, the tension T no longer exists and thus the elastic web 110 contracts to a normal relaxed state. As the elastic web 110 contracts to a normal relaxed state in the discharge area 136, extensible regions 138 are formed.

The extensible regions 138 are separated by inextensible regions 140. The inextensible regions 140 are created when the gripping nip 104 is in an open state. The elastic web 110 experiences no tension in the staging area 134 when the gripping nip 104 is in the open state (corresponding to when one of grooves 144 is aligned with and opposed to the roller 118). The size of the grooves 144 and ribs 142, in combination with the speed Sc of the gripping nip 104 determines the size of the extensible and inextensible regions 138 and 140.

Other means for gripping and releasing may be used. For example, one of the rollers of the gripping nip 104 may be pushed by a rotating cam, thereby moving the roller in and out of engagement with the opposing roller. In this embodiment, roller 120 could be smooth. Optionally, a roller from the gripping nip 104 may be physically moved in and out of the nip by an actuator, that could be electrically, pneumatically or hydraulically powered.

In FIG. 5, an adhesive coating station 111 is provided along the inelastic web 112, at which an adhesive coating is applied to one surface of the inelastic web 112. For example, the adhesive coating may be applied using spray or slot coating techniques. Optionally, the bonding nip 108 may perform thermal bonding, thermal point bonding, ultrasonic bonding, adhesive lamination, chemical bonding and the like.

In FIG. 5, the bonding nip 108 simultaneously functions to both draw in, and bond together, the elastic web 110 and inelastic web 112 at the bonding station 109. Optionally, the bonding station 109 may include two separate sets/pairs of rollers (e.g, a set defining a bonding nip and a set defining a drawing nip). One set of rollers would perform the drawing function and the other set of rollers would perform the bonding function. In this alternative embodiment, the elastic web 110 would first pass through the set of rollers performing the drawing function. Downstream of the drawing nip, the second set of rollers would be positioned to receive, and bond together, the elastic web 110 and inelastic web 112.

As a further alternative, the drawing nip may be positioned remote from the bonding station 109. The sets of rollers forming the drawing nip and bonding nip may be remotely spaced from one another in order that various other intervening processing steps may be performed.

The degree of elongation imparted to the elastic web 110 prior to entering the bonding nip 108 may be varied depending upon the degree of crepe induced extensibility that is desired of the inelastic web 112 in the garment to which it is applied. Typically this will be at least 50%, and optionally greater than 100%.

Similarly, in the event a grooved roller 120 is used in the gripping nip 104, the length of the inextensible region 140 will be a function of the length of the groove 144 around the circumference of the grooved roller 120 and the relative speeds of the gripping nip 104 and the bonding nip 108.

Figure 6:
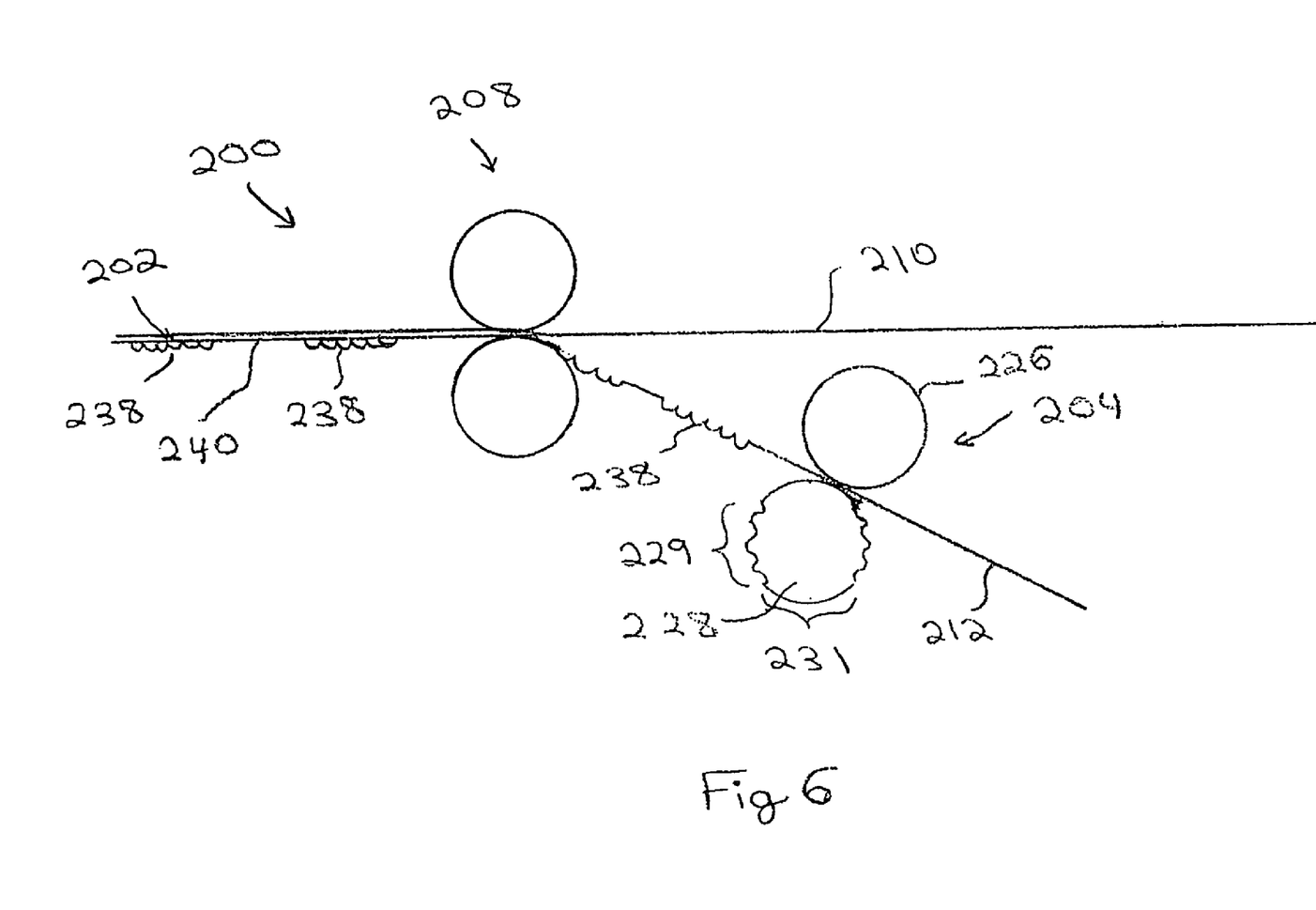
FIG. 6 illustrates an apparatus for producing a multi-layer web in accordance with an alternative embodiment.

FIG. 6 illustrates an alternative embodiment for an apparatus 200 that is configured to manufacture a laminated web 202 having extensible regions 238 and inextensible regions 240. The laminated web 202 is comprised of an elastic web 210 bonded to an inelastic web 212. The bonding operation is performed at a bonding nip 208. In the alternative embodiment of FIG. 6, the inelastic web 212 passes through a gripping nip 204 comprised of a smooth roller 226 and a creped roller 228. The creped roller 228 is configured with creping sections 229 and smooth sections 231 formed alternatively with one another about the circumference of the creped roller 228. The creping sections 229 are provided with a pattern of grooves and ribs forming a corrugated or creped pattern. As the creping sections 229 rotate into engagement with the inelastic web 212, a creped or corrugated pattern is formed in the inelastic web 212, which are subsequently bonded to the elastic web 210. The size and rotational speed of the smooth and creped rollers 226 and 228 may be varied as well as the circumferencial length and number of creping sections 229 and smooth sections 231 on the creped roller 228 in order to adjust the frequency, length and dimensions of the inextensible regions 238. Optionally, the smooth and/or creped rollers 226 and 228 may be heated.

In a further embodiment, the creping roller 208 may have grooves running axially along its length around all of its circumference. The elastic web would be forced into the grooves only in discrete regions corresponding to the extensible regions of the laminated web.

Figure 7:
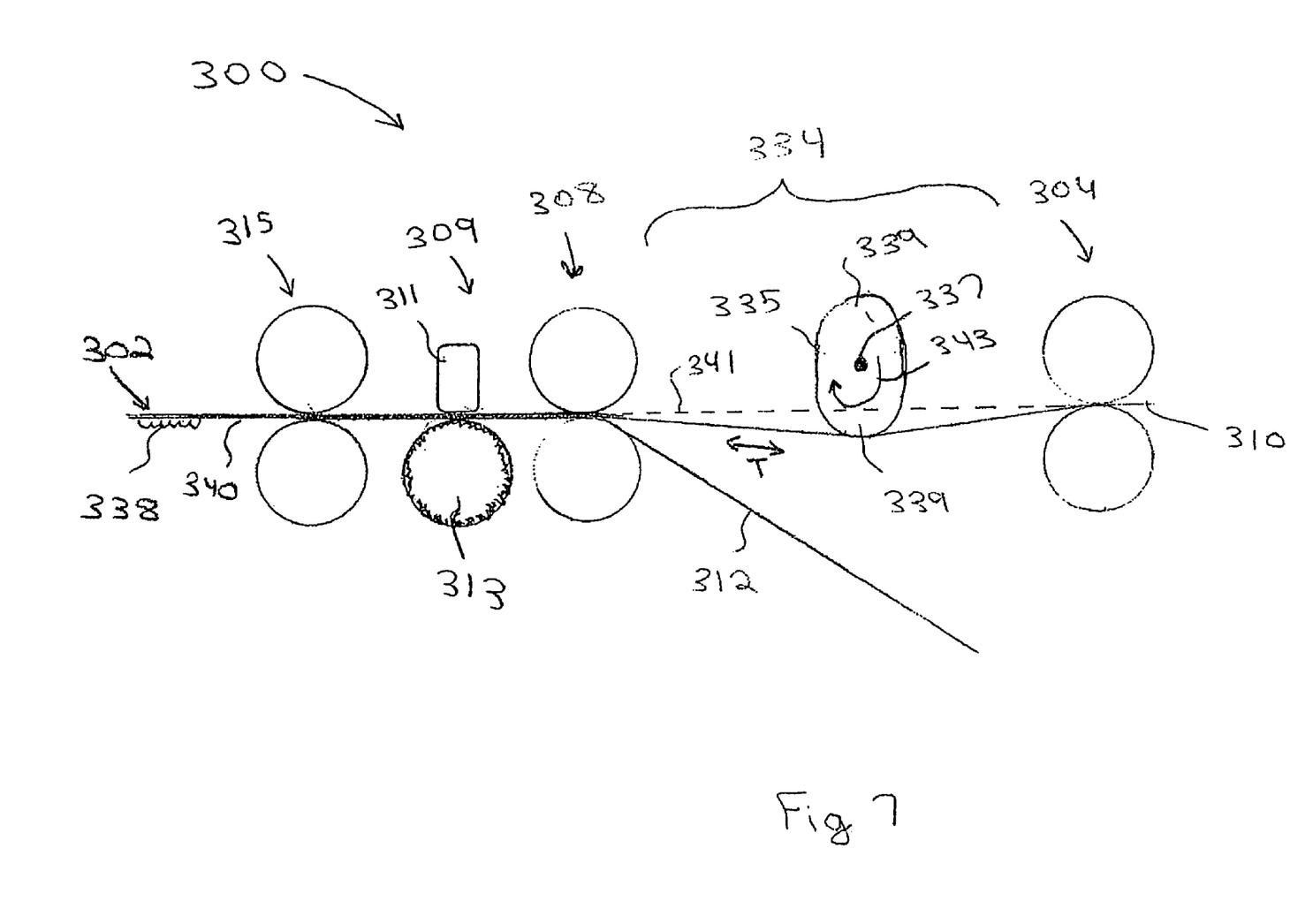
FIG. 7 illustrates an apparatus for producing a multi-layer web in accordance with an alternative embodiment.

FIG. 7 illustrates an alternative embodiment of an apparatus 300 configured to manufacture a multi-layer web 302 having extensible regions 338 and inextensible regions 340. The apparatus 300 includes a gripping nip 304, a drawing nip 308 and an ultrasonic bonding station 309. The gripping nip 304 and drawing nip 308 operate at the same circumferencial speed and are separated by a staging area 334 through which the elastic web 310 travels. Within staging area 334, a cam roller 335 is provided and configured to rotate about a cam axis 337. The cam roller 335 is positioned such that opposed cam sections 339 of the cam roller 335 move to a location within and extending through the machine path (denoted by dashed line 341) periodically as the cam roller 335 rotates. When one of the cam sections 339 is located within and extending through the machine path 341, the cam section 339 engages the elastic web 310 and introduces a tension T within the portion of the elastic web 310 located in the staging area 334 between the gripping nip 304 and bonding nip 308.

As the cam roller 335 continues to rotate in the direction denoted by arrow 343, the cam sections 339 move to positions remote from the elastic web 310, thereby removing any tension T from the elastic web 310 within the staging area 334. When the cam section 339 is located remote from the machining path 341, the elastic web 310 is permitted to return to a position extending along and co-extensive with the machine path 341. When the elastic web 310 is located along the machine path 341, no tension T exists within the elastic web 310. In the example of FIG. 7, cam sections 339 are located on opposite ends of the cam roller 335 such that, during one rotation of the cam roller 335, two separate cam sections 339 engage and deflect the elastic web 310 in connection with the formation of two successive extensible regions 338. During each rotation or cycle of the cam roller 335, the elastic web 310 is placed under tension at two separate portions of the cycle and released during two separate portions of the cycle.

The ultrasonic bonding station 309 is provided downstream of the drawing nip 308. The ultrasonic bonding station 309 includes an ultrasonic horn 311 positioned adjacent a textured bonding roller 313, between which the elastic and inelastic webs 310 and 312 pass. The ultrasonic horn 311 bonds (e.g., fuses) the elastic and inelastic webs 310 and 312 to one another at desired regions. The textured bonding roller 313 includes raised sections that define the points and/or regions at which bonding (e.g., fusion or ultrasonic welding) occurs. An outgoing nip 315 is provided downstream of the ultrasonic bonding station 309. The outgoing nip 315 rotates at the same circumferential speed as the drawing nip 308 which also functions as an incoming nip. The drawing and outgoing nips 308 and 315 cooperate to convey the elastic and inelastic webs 310 and 312 at the same relative speed through the ultrasonic bonding station 309. Among other things, the drawing and outgoing nips 308 and 315 cooperate to avoid slippage or relative motion between the elastic and inelastic webs 310 and 312 in the ultrasonic bonding station 309.

In a further embodiment, the tension in the elastic web may be varied by a means for varying the temperature of the elastic web. As an example of a means for varying the temperature of the elastic web, a controlled variation in temperature as the elastic web passes over the roller. In a still further embodiment, the tension in the elastic web may be varied by changing the conveying speed of the elastic web through the staging area prior to entry of the elastic web into the bonding nip 208 (308?). The elastic web may extend around the entire garment or maybe deadened or missing in the front and/or back of the garment.

Optionally, the inelastic web may be replaced with a partially elastic web, where the partially elastic web is less elastic than the elastic web joined thereto.

The elastic web may be made from any suitable elastic material, such as natural or synthetic polymeric materials. Examples of suitable polymers include low crystallinity polyethylenes, metallocene catalyzed low crystallinity polyethylene, ethylene vinyl acetate copolymers (EVA), polyurethane, polyisoprene, polyurethane, polyisoprene, butadiene-styrene copolymers, styrene block copolymers such as styrene/isoprene/styrene (SIS), styrene/butadiene/styrene (SBS), or styrene/ethylene-butadiene/styrene (SEBS) block copolymers. Blends of these polymers alone or with other modifying elastic or non-elastomeric materials may also be used. The elastomeric materials may comprise high performance elastomeric materials such as elastomeric block copolymer. An example of a suitable elastomeric block copolymer is sold under the brand name KRATON®, a registered trademark of the Kraton Polymers U.S. LLC.

While the description of the present invention presented above has been limited to certain embodiments, it will be obvious to those skilled in the art that various changes and modifications can be made without departing from the spirit and scope of the present invention, and all such variations and modifications are intended to be covered in the claims appended hereto. All such modifications are within the scope of this invention.

While the invention has been described in terms of various specific embodiments, those skilled in the art will recognize that the invention can be practiced with modification within the spirit and scope of the claims.

What is claimed is:

1. A method for manufacturing a multi-layer web, comprising;
    feeding first and second webs along a machine direction to a bonding station, the second web being elastic; and
    bonding the first and second webs to one another at the bonding station while alternately increasing and decreasing tension in said second web to create extensible regions corresponding to areas where the first and second webs are bonded together while the second web was stretched and inextensible regions corresponding to areas where the first and second webs are bonded together while the second web was not stretched, wherein the extensible and inextensible regions are arranged along the machine direction.

2. The method of claim 1, wherein the second web is alternately gripped and released between a pair of rollers located upstream of the bonding station, the rollers traveling at a circumferential speed that differs from a speed at which the first web is fed to the bonding station.

3. The method of claim 1, wherein alternately increasing and decreasing tension in the second web comprises changing a speed at which the second web is fed to the bonding station.

4. The method of claim 1, wherein alternately increasing and decreasing tension in the second web comprises gripping the second web with a cam roller that is driven in and out of a feed path along which the second web travels through a staging area.

5. The method of claim 1, wherein the bonding comprises one of thermal bonding, mechanical bonding, adhesive lamination, chemical bonding, ultrasonic bonding and any combination thereof.

* * * * *